(12) United States Patent
Johnson et al.

(10) Patent No.: US 11,710,361 B2
(45) Date of Patent: Jul. 25, 2023

(54) ENHANCED AUTHORIZATION TO ACCESS TRANSPORTATION HUB SERVICES

(71) Applicants: Matthew Johnson, Linkwood, MD (US); Dalibor Panic, Dublin (IE); Gordon Flood, Trim (IE); James Ahern, Dunboyne (IE); Martin Patefield-Smith, Cheltenham (GB)

(72) Inventors: Matthew Johnson, Linkwood, MD (US); Dalibor Panic, Dublin (IE); Gordon Flood, Trim (IE); James Ahern, Dunboyne (IE); Martin Patefield-Smith, Cheltenham (GB)

(73) Assignee: Daon Technology, Dublin (IE)

( * ) Notice: Subject to any disclaimer, the term of this patent is extended or adjusted under 35 U.S.C. 154(b) by 79 days.

(21) Appl. No.: 17/122,179

(22) Filed: Dec. 15, 2020

(65) Prior Publication Data

US 2022/0189226 A1   Jun. 16, 2022

(51) Int. Cl.
| | |
|---|---|
| *G07C 9/21* | (2020.01) |
| *G16H 10/60* | (2018.01) |
| *G07C 9/27* | (2020.01) |
| *G06Q 10/02* | (2012.01) |
| *G06Q 50/30* | (2012.01) |

(52) U.S. Cl.
CPC .............. *G07C 9/21* (2020.01); *G06Q 10/02* (2013.01); *G07C 9/27* (2020.01); *G16H 10/60* (2018.01); *G06Q 50/30* (2013.01)

(58) Field of Classification Search
CPC . G07C 9/21; G07C 9/27; G06Q 10/02; G06Q 50/30; G16H 10/60
See application file for complete search history.

(56) References Cited

U.S. PATENT DOCUMENTS

| | | | |
|---|---|---|---|
| 2010/0250290 A1* | 9/2010 | Lefkowitz | G06Q 30/0603 705/17 |
| 2016/0055698 A1 | 2/2016 | Gudmundsson et al. | |
| 2021/0328801 A1* | 10/2021 | Sly | H04L 9/0894 |

FOREIGN PATENT DOCUMENTS

GB    2 501 144    10/2013

OTHER PUBLICATIONS

Extended European Search Report for EPO Application No. 21208351.3, dated May 6, 2022, pp. 1-6.

* cited by examiner

*Primary Examiner* — Vernal U Brown
(74) *Attorney, Agent, or Firm* — Kevin McDermott, Esq.

(57) ABSTRACT

A method for enhanced authorization to access transportation hub services is provided that includes creating, by an electronic device, a token based on credentials of a traveler. Moreover, the method includes displaying the token by the electronic device for scanning for accessing a security service area and determining whether the credentials are valid. In response to determining the credentials are valid, a traveler operating the electronic device is authorized to access the security service area. Otherwise, the traveler is denied access to the security service area.

18 Claims, 7 Drawing Sheets

ENHANCED AUTHORIZATION TO ACCESS TRANSPORTATION HUB SERVICES

BACKGROUND OF THE INVENTION

This invention relates generally to transportation hub services, and more particularly, to enhanced authorization to access transportation hub services.

Travelers are known to wait in lengthy time-consuming queues in transportation hubs while traveling for business and recreation. Queue lengths vary with fluctuating traveler volumes, traveler behavior, and resource constraints of transportation hubs, and are known to be particularly burdensome for travelers during or around holiday seasons and during inclement weather. Such burdensome queues may cause travelers to miss, for example, an airplane flight and perhaps a connecting flight resulting in inconvenient, frustrating delays. Additionally, hotels and individuals planning to collect the traveler may need to be notified of delays.

Because travelers are typically close to each other in such queues, travelers are more likely to contract pathogens from each other while in the queue. Such queue conditions may thus present a dangerous health risk for travelers who are vulnerable to lethal pathogens like the coronavirus.

Currently, transportation hub operators use historical traveler data to predict the timing of daily, weekly, and holiday traveler volume surges and allocate resources according to the predictions. However, despite the best efforts of transportation hub operators overcrowded queues continue to develop. Therefore, known techniques for managing transportation hub queues have drawbacks.

Thus, it would be advantageous and an improvement over the relevant technology to provide an apparatus, method and computer-readable readable recording medium capable of enhancing authorization to access transportation hub services to reduce traveler inconvenience and reduce health risks for travelers.

BRIEF DESCRIPTION OF THE INVENTION

An aspect of the present disclosure provides a method for enhanced authorization to access transportation hub services that includes creating, by an electronic device, a token based on credentials of a traveler. Moreover, the method includes displaying the token by the electronic device for scanning for accessing a security service area and determining whether the credentials are valid. In response to determining the credentials are valid, the traveler is authorized to access the security service area. Otherwise, the traveler is denied access to the security service area.

An aspect of the present disclosure provides an electronic device for enhancing authorization to access transportation hub services that includes a processor and a memory configured to store data. The electronic device is associated with a network and the memory is in communication with the processor and has instructions stored thereon which, when read and executed by the processor, cause the electronic device to create a token based on credentials of a traveler, display the token for scanning for accessing a security service area, and determine whether the credentials are valid. Moreover, the instructions, when read and executed by the processor, cause the electronic device to authorize the traveler to access the security service area in response to determining the credentials are valid, and deny the traveler access to the security service area in response to determining at least one of the credentials is invalid.

An aspect of the present disclosure provides a non-transitory computer-readable recording medium in an electronic device for enhancing authorization to access transportation hub services. The non-transitory computer-readable recording medium stores instructions which when executed by a hardware processor cause the non-transitory recording medium to perform steps including creating a token based on credentials of a traveler, displaying the token for scanning for accessing a security service area, and determining whether the credentials are valid. Moreover, the instructions which when executed by the hardware processor cause the non-transitory recording medium to perform steps including authorizing the traveler to access the security service area in response to determining the credentials are valid, and denying the traveler access to the security service area in response to determining at least one of the credentials is invalid.

DETAILED DESCRIPTION OF THE INVENTION

The following detailed description is made with reference to the accompanying drawings and is provided to assist in a comprehensive understanding of various example embodiments of the present disclosure. The following description includes various details to assist in that understanding, but these are to be regarded merely as examples and not for the purpose of limiting the present disclosure as defined by the appended claims and their equivalents. The words and phrases used in the following description are merely used to enable a clear and consistent understanding of the present disclosure. In addition, descriptions of well-known structures, functions, and configurations may have been omitted for clarity and conciseness. Those of ordinary skill in the art will recognize that various changes and modifications of the examples described herein can be made without departing from the spirit and scope of the present disclosure.

Figure 1:
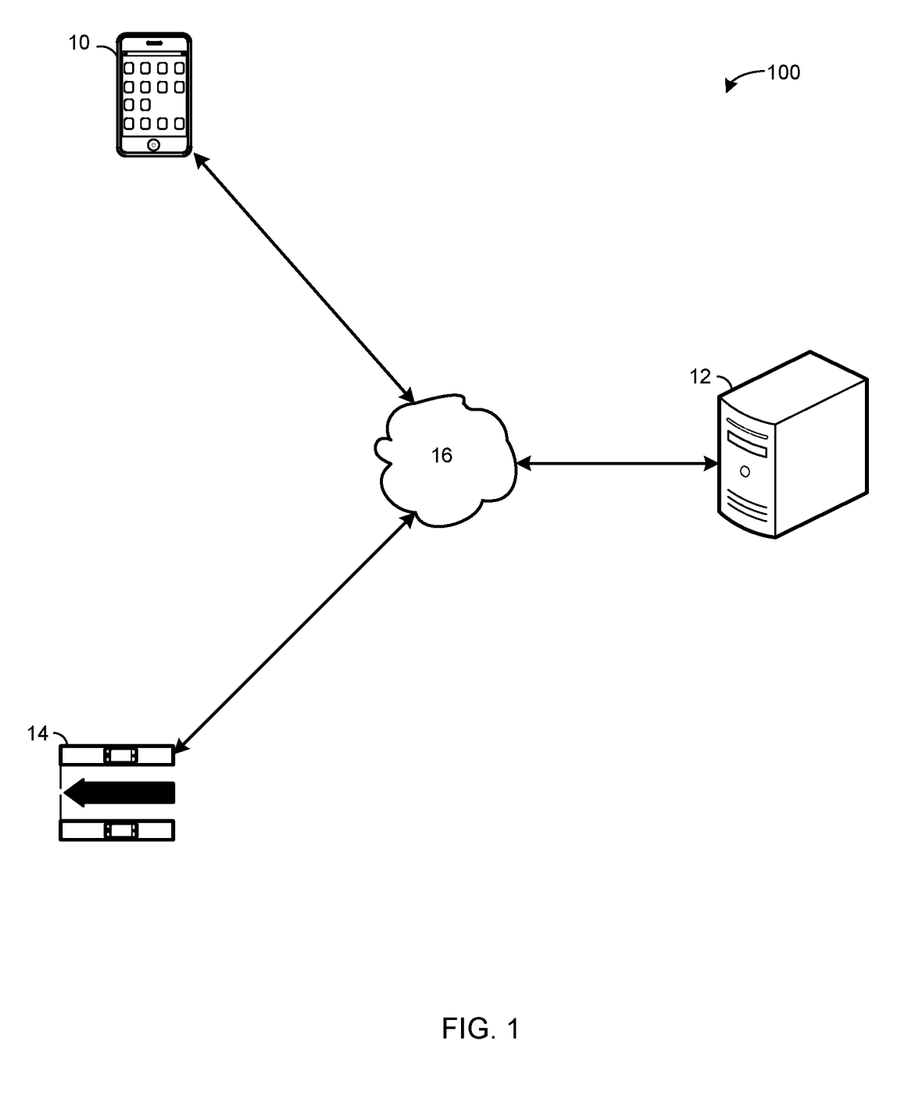
FIG. 1 is a schematic diagram of an example computing system used for enhancing authorization to access transportation hub services according to an embodiment of the present disclosure.

FIG. 1 is a schematic diagram of an example computing system 100 for enhancing authorization to access transportation hub services according to an embodiment of the present disclosure. As shown in FIG. 1, the main elements of the system 100 include a computing device 10, a computer 12, and an access control mechanism (ACM) 14 communicatively connected via a network 16.

In FIG. 1, the computing device 10 can be any wireless hand-held electronic consumer computing device capable of at least downloading applications over the Internet, running the applications, capturing and storing data temporarily and/or permanently, and otherwise performing any and all functions described herein by any computer, computer system, or computing device included in the system 100. One example of the computing device 10 is a smart phone. Other examples include, but are not limited to, a cellular phone, a tablet computer, a phablet computer, a laptop computer, and any type of hand-held consumer electronic device having wired or wireless networking capabilities capable of performing the functions, methods, and/or algorithms described herein. Although the system 100 includes a single computing device 10, it is contemplated by the present disclosure that the system 100 may include any number of computing devices 10. Each computing device 10 is typically associated with a single traveler as described herein. However, it is contemplated by the present disclosure that each computing device 10 may alternatively be associated with more than one traveler, for example, a husband and wife.

The computer 12 can be, for example, any type of server or computer implemented as a network server or network computer. The computing device 10 and computer 12 may alternatively be referred to as electronic devices or information systems.

The ACM 14 can be any automated self-service barrier which can obtain data stored in a chip of a document to verify a traveler's identity. For example, biometric template data stored in the chip may be obtained and used to biometrically verify the identity of the traveler. One example of an ACM 14 is an electronic gate (eGate). After a traveler is successfully authenticated, a physical barrier such as a gate or turnstile opens to permit passage.

The network 16 may be implemented as a 5G communications network. Alternatively, the network 16 may be implemented as any wireless network including, but not limited to, 4G, 3G, Wi-Fi, Global System for Mobile (GSM), Enhanced Data for GSM Evolution (EDGE), and any combination of a LAN, a wide area network (WAN) and the Internet. The network 16 may also be any type of wired network or a combination of wired and wireless networks.

It is contemplated by the present disclosure that the number of computing devices 10, computers 12, and ACMs 14 is not limited to the number of computing devices 10, computers 12, and ACMs 14 shown in FIG. 1.

Figure 2:
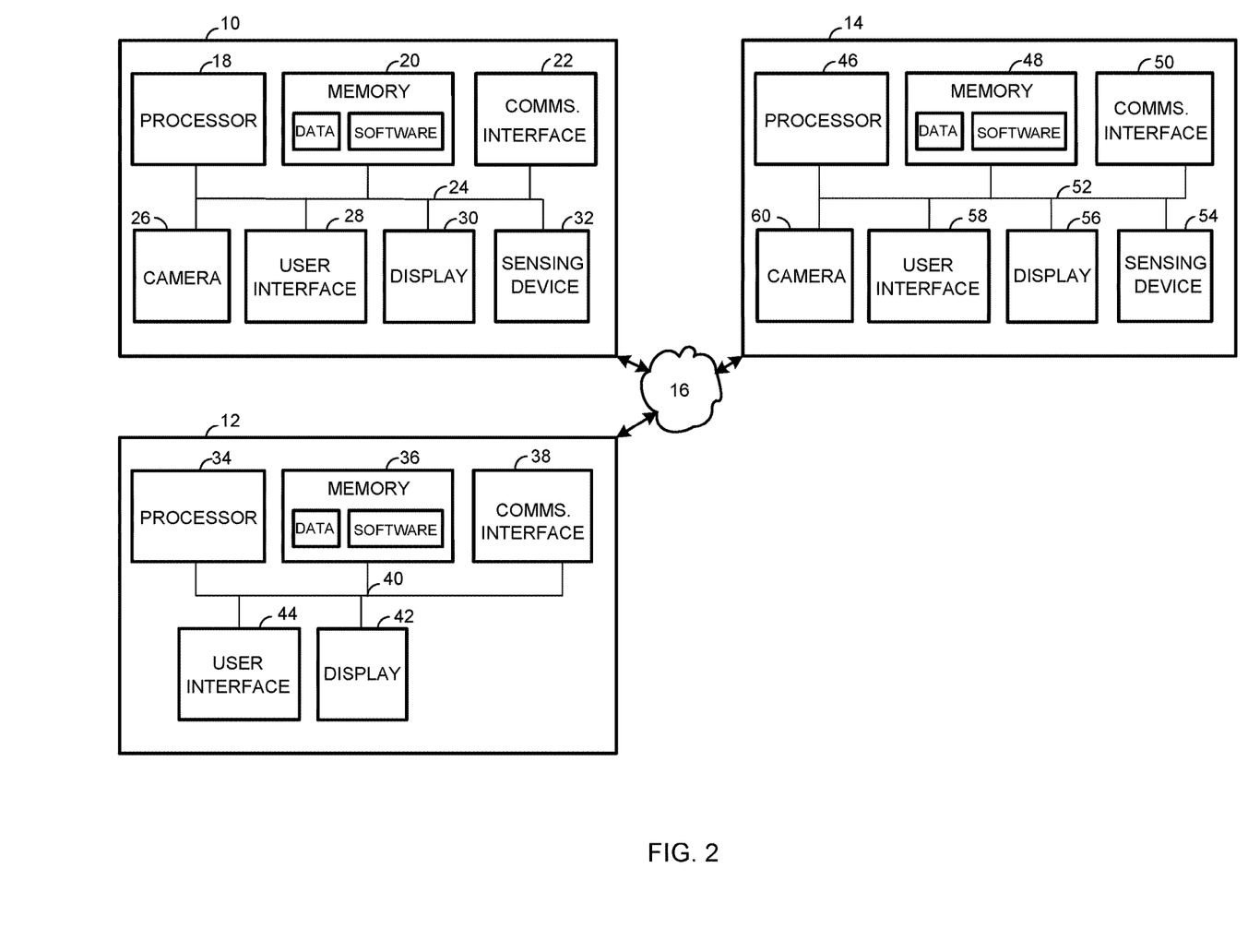
FIG. 2 is a more detailed schematic diagram illustrating the computing device, computer, and access control mechanism (ACM) in the system of FIG. 1.

FIG. 2 is a more detailed schematic diagram illustrating the computing device 10, the computer 12, and the ACM 14 in the system 100 for enhancing authorization to access transportation hub services according to an embodiment of the present disclosure. Transportation hub services include, but are not limited to, security services and modes of transportation. Although FIG. 2 shows one computing device 10, one ACM 14, and one computer 12, the computing device 10, the ACM 14, and the computer 12 in the figure are meant to be representative of additional computing devices 10, ACMs 14, and computers 12 that may be included in the system 100 shown in FIG. 1.

The computing device 10 includes components such as, but not limited to, one or more processors 18, a memory 20, a communications interface 22, a bus 24, a camera 26, a user interface 28, a display 30, and a sensing device 32. General communication between the components in the computing device 10 is provided via the bus 24.

The processor 18 executes software instructions, or computer programs, stored in the memory 20. As used herein, the term processor is not limited to just those integrated circuits referred to in the art as a processor, but broadly refers to a computer, a microcontroller, a microcomputer, a programmable logic controller, an application specific integrated circuit, and any other programmable circuit capable of executing at least a portion of the functions and/or methods described herein. The above examples are not intended to limit in any way the definition and/or meaning of the term "processor."

The memory 20 may be any non-transitory computer-readable recording medium. Non-transitory computer-readable recording media may be any tangible computer-based device implemented in any method or technology for short-term and long-term storage of information or data. Moreover, the non-transitory computer-readable recording media may be implemented using any appropriate combination of alterable, volatile or non-volatile memory or non-alterable, or fixed, memory. The alterable memory, whether volatile or non-volatile, can be implemented using any one or more of static or dynamic RAM (Random Access Memory), a floppy disc and disc drive, a writeable or re-writeable optical disc and disc drive, a hard drive, flash memory or the like. Similarly, the non-alterable or fixed memory can be implemented using any one or more of ROM (Read-Only Memory), PROM (Programmable Read-Only Memory), EPROM (Erasable Programmable Read-Only Memory), EEPROM (Electrically Erasable Programmable Read-Only Memory), and disc drive or the like. Furthermore, the non-transitory computer-readable recording media may be implemented as smart cards, SIMS, any type of physical and/or virtual storage, or any other digital source such as a network or the Internet from which a computing device can read computer programs, applications or executable instructions.

The memory 20 may be used to store any type of data, for example, data records of travelers. The data records are typically for travelers associated with the computing device 10. The data record for each traveler may include data such as, but not limited to, health credentials, reservation credentials, electronic tokens, health questionnaires, messages for prompting travelers to perform an action, biometric modality data, biometric templates, and personal data. Biometric modality data is the data of a biometric modality of a person captured by the computing device 10. Biometric modalities include, but are not limited to, voice, face, finger, iris, palm, any other modalities, and any combination of modalities. Biometric modality data may be in any form including, but not limited to, image data and audio data. Image data may be a digital image, a sequence of digital images, or a video. Each digital image is included in a frame. The biometric modality data in the data record may be processed to generate at least one biometric modality template. The memory 20 may also store an identifier of the computing device 10. The identifier may include all numbers, all letters, or may be alphanumeric and may be of any length.

Biometric modality data may be captured in any manner. For example, for voice biometric data the computing device 10 may record a user speaking. For face biometric data, the camera 26 may record image data of the face of a user by taking one or more photographs or digital images of the user, or by taking a video of the user. The camera 26 may record a sequence of digital images at irregular or regular intervals. A video is an example of a sequence of digital images being captured at a regular interval. Captured biometric modality data may be temporarily or permanently stored in the computing device 10 or in any device capable of communicating with the computing device 10 via the network 16. As used herein, capture means to record temporarily or permanently, any data including, for example, biometric modality data of a person.

The process of verifying the identity of a user is known as a verification transaction. Typically, during a verification transaction a biometric template is generated from biometric modality data of a user captured during the transaction. The generated biometric template is compared against the corresponding record biometric template of the user and a matching score is calculated for the comparison. If the matching score meets or exceeds a threshold score, the identity of the user is verified as true. Alternatively, the captured user biometric modality data may be compared against the corresponding record biometric modality data to verify the identity of the user. An authentication data requirement is the biometric modality data desired to be captured during a verification or identification transaction.

The term "personal data" as used herein includes any demographic information regarding a traveler as well as contact information pertinent to the traveler. Such demographic information includes, but is not limited to, a traveler's name, age, date of birth, street address, email address, citizenship, marital status, and contact information. Contact information can include devices and methods for contacting the traveler.

Additionally, the memory 20 can be used to store any type of software. As used herein, the term "software" is intended to encompass an executable computer program that exists permanently or temporarily on any non-transitory computer-readable recordable medium that causes the computing device 10 to perform at least a portion of the functions, methods, and/or algorithms described herein. Application programs are software and include, but are not limited to, operating systems, Internet browser applications, enrolment applications, a travel related application, and any other software and/or any type of instructions associated with algorithms, processes, or operations for controlling the general functions and operations of the computing device 10. The travel application can be downloaded from a digital distribution service via the network 16 using the computing device 10 or similar device. The software may also include computer programs that implement buffers and use RAM to store temporary data.

When executed by the processor 18, the travel related application causes the computing device 10 to perform operations such as, but not limited to, capturing personal data about a traveler, capturing answers to a health questionnaire, creating a health credential for a traveler, creating a reservation credential for a traveler, creating an electronic token based on the health and reservation credentials for a traveler, displaying the electronic token, displaying an icon that includes a message for performing an action, determining whether or not a health credential was created within a period of time, and determining whether or not a reservation credential is for a current time. One example of the message is "Show QR Code".

The communications interface 22 may include various network cards, and circuitry implemented in software and/or hardware to enable wired and/or wireless communications with other computing devices 10 (not shown), the computer 12, and the ACM 14 via the network 16. Communications include, for example, conducting cellular telephone calls and accessing the Internet over the network 16. By way of example, the communications interface 22 may be a digital subscriber line (DSL) card or modem, an integrated services digital network (ISDN) card, a cable modem, or a telephone modem to provide a data communication connection to a corresponding type of telephone line. As another example, the communications interface 22 may be a local area network (LAN) card (e.g., for Ethernet™ or an Asynchronous Transfer Model (ATM) network) to provide a data communication connection to a compatible LAN. As yet another example, the communications interface 22 may be a wire or a cable connecting the computing device 10 with a LAN, or with accessories such as, but not limited to, other computing devices. Further, the communications interface 22 may include peripheral interface devices, such as a Universal Serial Bus (USB) interface, a PCMCIA (Personal Computer Memory Card International Association) interface, and the like.

The communications interface 22 also allows the exchange of information across the network 16. The exchange of information may involve the transmission of radio frequency (RF) signals through an antenna (not shown). Moreover, the exchange of information may be between the computing device 10, other computing devices 10 (not shown), the computer 12, the ACM 14, and other computer systems (not shown) capable of communicating over the network 16.

Examples of other computer systems (not shown) include computer systems of service providers such as, but not limited to, financial institutions, medical facilities, national security agencies, merchants, and authenticators. The computing devices 10 (not shown) may be associated with any traveler or with any type of entity including, but not limited to, commercial and non-commercial entities.

The camera 26 captures image data. The camera 26 can be one or more imaging devices configured to record image data of at least a portion of the body of a traveler including any biometric modality of the traveler while utilizing the computing device 10. Moreover, the camera 26 is capable of recording image data under any lighting conditions including infrared light. The camera 26 may be integrated into the computing device 10 as one or more front-facing cameras and/or one or more rear facing cameras that each incorporates a sensor, for example and without limitation, a CCD or CMOS sensor. Alternatively, the camera 26 can be external to the computing device 10.

The user interface 28 and the display 30 allow interaction between a traveler and the computing device 10. The display 30 may include a visual display or monitor that displays information to a traveler. For example, the display 30 may be a Liquid Crystal Display (LCD), active matrix display, plasma display, or cathode ray tube (CRT). The user interface 28 may include a keypad, a keyboard, a mouse, an illuminator, a signal emitter, a microphone, and/or speakers.

Moreover, the user interface 28 and the display 30 may be integrated into a touch screen display. Accordingly, the display may also be used to show a graphical user interface, which can display various data and provide "forms" that include fields that allow for the entry of information by the user. Touching the screen at locations corresponding to the display of a graphical user interface allows the person to interact with the computing device 10 to enter data, change settings, control functions, etc. Consequently, when the touch screen is touched, the user interface 28 communicates this change to the processor 18, and settings can be changed or user entered information can be captured and stored in the memory 20. The display 30 may function as an illumination source to apply illumination to an object while image data for the object is captured.

For user interfaces 28 that include an illuminator, the illuminator may project visible light, infrared light or near infrared light on a biometric modality, and the camera 26 may detect reflections of the projected light off the biometric modality. The reflections may be off of any number of points on the biometric modality. The detected reflections may be communicated as reflection data to the processor 18 and the memory 20. The processor 18 may use the reflection data to create at least a three-dimensional model of the biometric modality and a sequence of two-dimensional digital images. For example, the reflections from at least thirty thousand discrete points on the biometric modality may be detected and used to create a three-dimensional model of the biometric modality. Alternatively, or additionally, the camera 26 may include the illuminator.

The sensing device 32 may include Radio Frequency Identification (RFID) components or systems for receiving information from other devices in the system 100 and for transmitting information to other devices in the system 100. The sensing device 32 may alternatively, or additionally, include components with Bluetooth, Near Field Communication (NFC), infrared, or other similar capabilities.

The computer 12 can be, for example, any type of server or computer implemented as a network server or network computer and can include components similar those described herein with reference to the computing device 10. More specifically, the computer 12 can include components such as, but not limited to, one or more processors 34, a memory 36, a communications interface 38, a bus 40, a display 42, and a user interface 44. General communication between the components in the computer 12 is provided via the bus 40.

The processor 34 is similar to the processor 18 described herein with regard to the computing device 10. Additionally, the memory 36 is similar to the memory 20 described herein with regard to the computing device 10. However, the non-alterable or fixed memory can additionally be implemented using an optical ROM disc, such as a CD-ROM or DVD ROM disc. The memory 36 may be used to store any type of data, for example, traveler data records similar to those described herein for the memory 20. Furthermore, the memory 36 can be used to store any type of software including, for example, the software described herein as being stored in the memory 20.

The user interface 44 is similar to the user interface 28 described herein with regard to the computing device 10. Moreover, the display 42 and communications interface 38 are similar to the display 30 and communications interface 22, respectively, described herein with regard to the computing device 10.

The ACM 14 can be any automated self-service barrier which can obtain data stored in a chip of a document and can transmit the obtained data to a computer system, for example, computer 12 which verifies the identity of the traveler based on the obtained data. Alternatively, the ACM 14 may verify the identity of the traveler using the obtained data. For example, biometric template data stored in the chip of a document may be obtained and used to biometrically verify a traveler's identity. One example of an ACM is an electronic gate (eGate). The document can be a government issued document, for example, a passport or a driving license.

The data can be obtained from the chip using RFID, Bluetooth, NFC, infrared, or other similar capabilities. After the identity of a traveler is successfully verified, a physical barrier such as a gate or turnstile opens to permit passage into, for example, a security service area.

The ACM 14 can include components such as, but not limited to, one or more processors 46, a memory 48, a communications interface 50, a bus 52, a sensing device 54, a display 56, a user interface 58, and a camera 60. General communication between the components in the ACM 14 is provided via the bus 52.

The processor 46 and memory 48 are similar to the processor 18 and memory 20, respectively, described herein with regard to the computing device 10. Additionally, the memory 48 may be used to store any type of data, for example, data of a biometric modality captured during a verification transaction, data of a biometric modality of a traveler obtained from a document presented by the traveler, and personal data about travelers. Furthermore, the memory 40 can be used to store any type of software including the software described herein as being stored in the memory 20 as well as, for example, software for conducting verification transactions.

The communications interface 50, sensing device 54, and display 56 are similar to the communications interface 22, sensing device 32, and display 30, respectively, described herein with regard to the computing device 10. The camera 60 may be similar to the camera 26 in the computing device 10 or may be any camera suitable for capturing data of a biometric modality of travelers.

The user interface 58 can be similar to the user interface 28 described herein with regard to the computing device 10. Additionally, the user interface 58 includes a scanner for scanning documents presented by travelers. As a result of scanning a document, for example, a passport the ACM 14 can capture data about the traveler associated with the passport. The ACM 14 may also scan electronic tokens displayed by the computing device 10 of a traveler, and the scanned token and/or data related to the token may be communicated to another device included in the system 100, for example, the computer 12.

It is contemplated by the present disclosure that transportation hubs can be any facility that accommodates a mode of transportation and include, but are not limited to, airports, train stations, and bus depots. Transportation hub services include, but are not limited to, checkpoint security services and modes of transportation. Modes of transportation include, but are not limited to, airplanes, trains, subways, taxis, transportation computer company autos, and buses.

Figure 3:
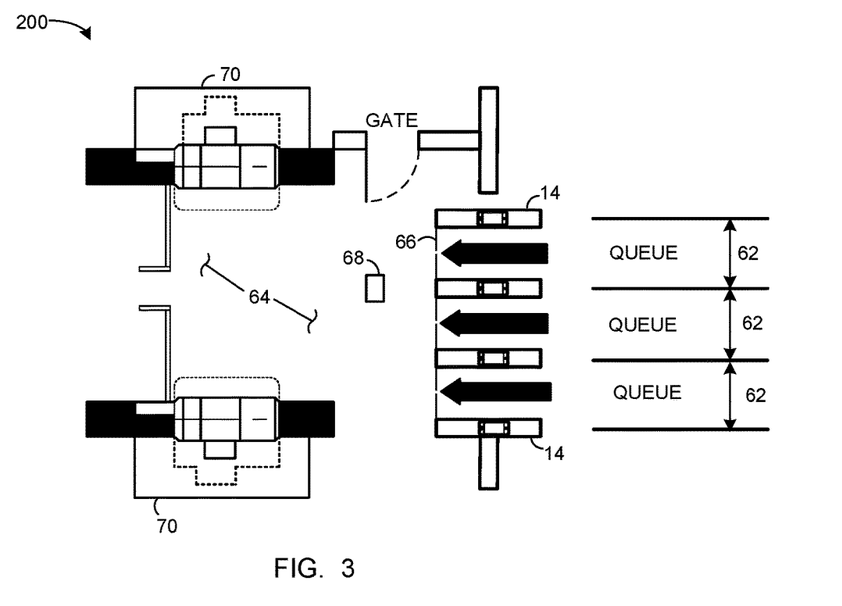
FIG. 3 is a top view of an example security checkpoint including ACMs.

FIG. 3 is a top view of an example security checkpoint 200 that can be found in a transportation hub. The security checkpoint 200 can include, for example, ACMs 14, a lane or aisle 62 corresponding to each ACM 14, and a security service area 64. The ACMs 14 may each include a mechanism 66 for preventing travelers from entering the security service area 64. Such mechanisms 66 include, but are not limited to, a turnstile, an electronic door, and a swing gate.

Each lane or aisle 62 accommodates a queue of travelers desiring to pass through a respective ACM 14 to access the security service area 64. The security service area 64 includes a walk-through metal detector 68 for screening travelers and X-ray machines 70 for screening traveler carry-on items.

Figure 4:
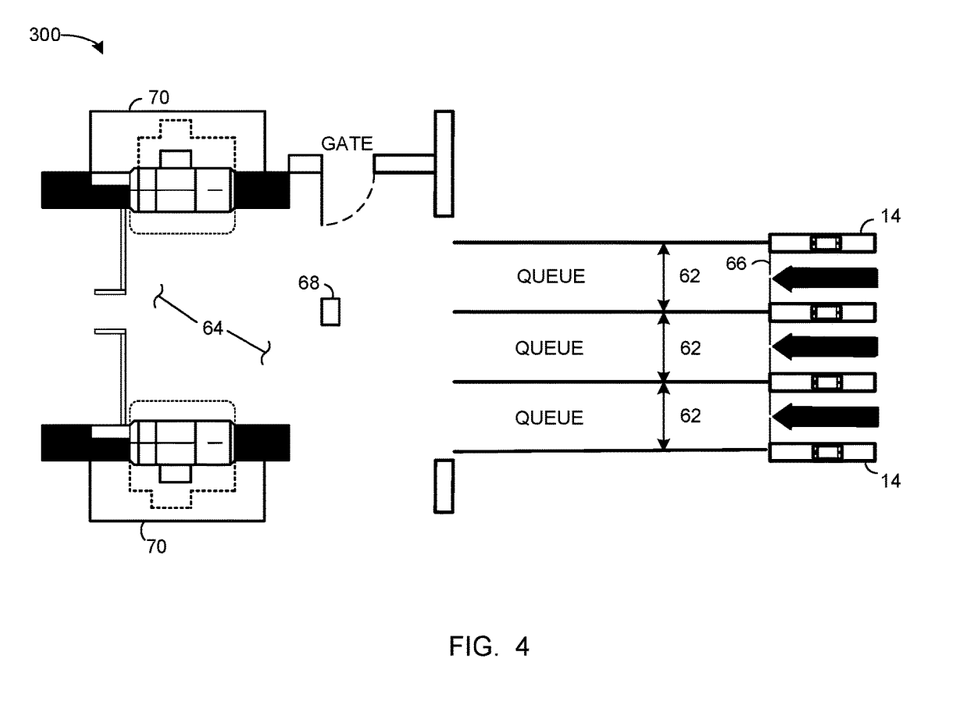
FIG. 4 is a top view of the security checkpoint shown in FIG. 3 with the ACMs in a different location.

The information shown in FIG. 4 is the same information shown in FIG. 3 as described in more detail below. As such, features illustrated in FIG. 4 that are identical to features illustrated in FIG. 3 are identified using the same reference numerals used in FIG. 3.

FIG. 4 is a top view of another example security checkpoint 300 similar to the checkpoint 200 shown in FIG. 3. However, the ACMs 14 are not located near the security checkpoint 64. Rather, each ACM 14 is located at the entrance to an aisle 62. Positioning each ACM 14 at the entrance to an aisle 62 allows identifying a traveler without a valid electronic token before the traveler enters a queue. Thus, the number of travelers in a queue is facilitated to be reduced. As a result, traveler delays, inconvenience, and frustration are facilitated to be reduced. Moreover, with fewer travelers in the queue it is easier to practice social distancing to facilitate reducing transmission of pathogens between travelers.

Travelers are known to wait in crowded lengthy time-consuming queues in order to access the security service area 64. Queue lengths vary with fluctuating traveler volumes, traveler behavior, and resource constraints of transportation hubs, and are known to be particularly burdensome for travelers during or around holiday seasons and during periods of inclement weather. Such burdensome queues may cause travelers to miss, for example, an airplane flight or a train resulting in inconvenient, frustrating delays. A missed flight may cause travelers to miss connecting flights or trains thus compounding delays, inconvenience and frustration for travelers.

Because travelers are typically close to each other in such queues, travelers are more likely to contract pathogens from each other while in the queue. Such queue conditions may thus present a dangerous health risk for travelers who are vulnerable to lethal pathogens like the coronavirus.

To address these problems, each traveler uses his or her computing device 10 to create and display an electronic token for scanning by the ACM 14. The ACM 14 can transmit the scanned token and/or data about the token, to the computer 12 which can determine whether or not the token is valid. If valid, the computer 12 transmits a message to the ACM 14 indicating the token is valid and the traveler associated with the token is authorized to pass through the ACM 14 and access the security service area 64. Otherwise, if the token is invalid a message is transmitted to the ACM 14 indicating the token is invalid and the traveler is not authorized to access the security service area 64.

In order to obtain an electronic token, each traveler can be required to obtain a health credential and a reservation credential before arriving at a transportation hub. Alternatively, travelers may obtain the credentials at the transportation hub, but before attempting to pass through an ACM 14. The health credential can be obtained by satisfactorily completing a health questionnaire which is a series of questions about the health of the traveler. The questions may enquire about, for example, whether the traveler has been tested for a pathogen and if so the result and date of the test. Additional questions may include, but are not limited to, whether the traveler has a fever and has been in contact with a person infected with a pathogen. If the traveler has been in contact with a person infected with a pathogen, another question may enquire about the length of time since contact. It is contemplated by the present disclosure that the questionnaire may include any number of questions and that any question relating to the health of a traveler may be included.

A traveler may use his or her computing device 10 to download the questionnaire over the network 16 and to answer the questions. The answers are transmitted to the computer 12 which determines if the traveler constitutes a health risk to other travelers based on the answers. After determining the traveler does not constitute a health risk, the computer 12 creates and can transmit an electronic health credential to the computing device 10 of the traveler.

A traveler is considered a risk to other travelers when an answer indicates he or she may transmit a pathogen like the coronavirus to others. For example, it is recommended that people who may have been in contact with an infected person quarantine for fourteen days. Thus, a person who answers that he or she was in contact with an infected person within fourteen days of the travel date is considered a health risk to others.

It is contemplated by the present disclosure that the health credential be created no more than twenty-four hours before a traveler attempts to access the security service area 64. Alternatively, the health credential may be created any period of time before attempting to access the security service area 64 that inhibits the spread of a pathogen like the coronavirus.

The computing device 10 of a traveler can also be used to obtain an electronic reservation credential. More specifically, a traveler can operate his or her computing device 10 to reserve a period of time to wait in a queue and access the security service area 64. The period of time may be, for example, fifteen minutes. Alternatively, the period of time may be of any duration that enables travelers to pass through the security checkpoint 200 without delay while ensuring social distancing and other health safety measures can be practiced. Such health safety measures include, but are not limited to, checking travelers for a fever. After reserving a period of time, the computer 12 creates and can transmit a reservation credential to the computing device 10 of the traveler. The reservation credential is valid during the reserved time only.

Figure 5:
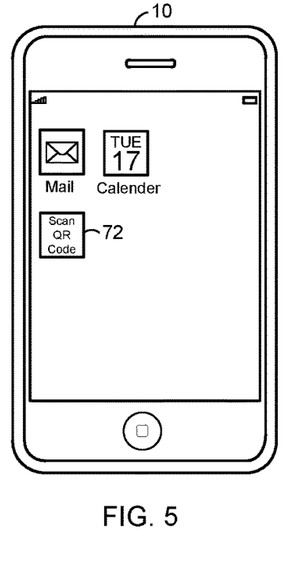
FIG. 5 is an enlarged plan view of the computing device displaying buttons and/or icons.

FIG. 5 is an enlarged plan view of the computing device 10 displaying buttons and/or icons. One button and/or icon 72 includes a message that reads "Scan QR Code". In response to the "Scan QR Code" icon 72 being pressed, touched or operated, the computing device 10 can create an electronic token based on the health credential and the reservation credential of the traveler. The token can include the identifier of the traveler's computing device 10, the traveler's email address, and any other information relating to the traveler. Additionally, it is contemplated by the present disclosure that the electronic token may be any type of token, including, but not limited to, a QR code and a bar code. The created electronic token can also be displayed by the computing device 10. The displayed icon 72 is typically pressed, touched or operated when the traveler arrives at an ACM 14.

The traveler presents the displayed electronic token to the scanner in the ACM 14. After scanning the token, the ACM 14 transmits the scanned token and/or data about the token, to the computer 12 which determines whether or not the token is valid. If valid, the computer 12 transmits a message to the ACM 14 indicating the token is valid and the traveler associated with the token is authorized to access the security service area 64. As a result, the mechanism 66 operates to permit the traveler to enter the security service area 64. Additionally, the computing device 10 may display a message indicating the traveler is authorized to access the security service area when both credentials are valid.

Otherwise, if the token is invalid a message is transmitted to the ACM 14 indicating the token is invalid and the traveler is not authorized to access the security service area 64. As a result, the mechanism 66 does not operate to permit the traveler into the security service area 64. Additionally, the computing device 10 may display a message indicating the traveler is denied access to the security service area 64 when the token is invalid. The token is invalid when at least one of the health and reservation credentials is invalid.

Although the ACM 14 transmits the scanned token and/or data about the token to the computer 12 after scanning the electronic token, the ACM 14 may alternatively transmit the scanned token and/or data about the token to the computing device 10. Thus, it is contemplated by the present disclosure that the computing device 10 may alternatively determine whether or not the token is valid and as a result that the traveler is authorized or not authorized to access the area 64. The computing device 10 may transmit a message to the ACM 14 indicating the traveler is authorized or not authorized to access the area 64. After receiving the message, the ACM 14 operates the mechanism 66 according to the received message. Additionally, the computing device 10 may display a message indicating the traveler is authorized or not authorized to access the security service area 64.

Although the icon 72 includes a message that reads "Scan QR Code", the icon 72 may alternatively include a message that reads "Show QR Code" when the token is a QR code or "Scan the bar code" or "Show the Bar Code" when the token is a bar code. Instead of the electronic token being created by the computing device 10, in response to the icon 72 being touched, pressed or operated the computing device 10 may communicate with the computer 12 such that the computer 12 creates the electronic token and transmits the token to the computing device 10 for display. Although the message is displayed as part of an icon, it is contemplated by the present disclosure that the message may alternatively be displayed in any manner, for example, as large bold text across the display 30. For such a message, the electronic token may be created when the large bold text is touched or pressed.

Figure 6:
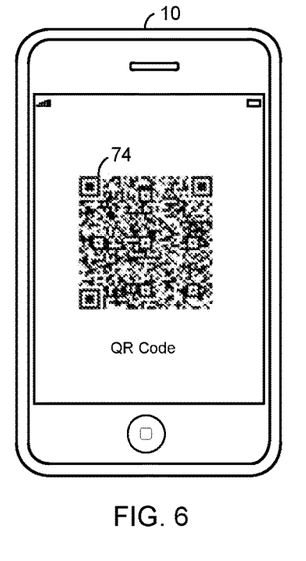
FIG. 6 is an enlarged plan view of the computing device displaying a QR Code.

FIG. 6 is an enlarged plan view of the computing device 10 displaying a QR Code 74 created in response to pressing, touching or operating the icon 72.

Figure 7:
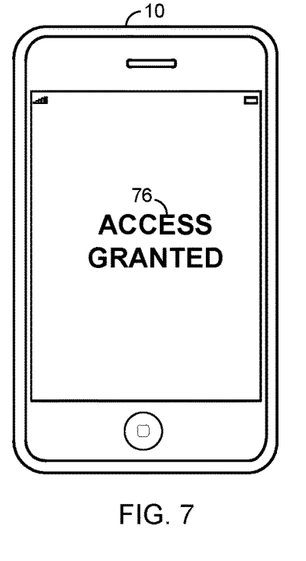
FIG. 7 is an enlarged plan view of the computing device displaying a message ACCESS GRANTED.

FIG. 7 is an enlarged plan view of the computing device 10 displaying a message "ACCESS GRANTED" 76 which indicates that the traveler is authorized to access the security service area 64. Alternatively, a message that reads "ACCESS DENIED" may be displayed when the traveler is not authorized to access the security service area 64. It is contemplated by the present disclosure that the computing device 10 may alternatively display any message that indicates the traveler is authorized or not authorized to access the security service area 64. Such messages may also be displayed when a traveler is authorized, or not authorized, respectively, to board a mode of transportation.

Figure 8:
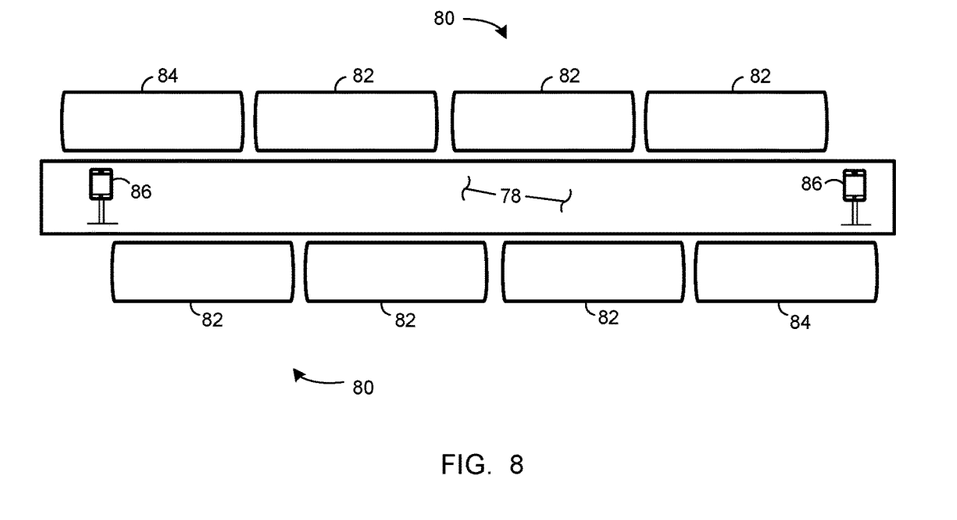
FIG. 8 is a top view of an example train platform including scanners and a train on each side of the platform.

FIG. 8 is a top view of an example train platform 78 including a train 80 on each side of the platform 78. Each train 80 includes standard cars 82 and a car 84 reserved for travelers who desire to practice social distancing from other travelers. The trains 80 may include any number of standard cars 82 and any number of reserved cars 84. Additionally, a scanner 86 can be located at the entry to each car 84. Some airports are known to use trains to transport people to and between terminals. Thus, it is contemplated by the present disclosure that the train platform 78 may be located in an airport or other transportation hub like a train station.

Travelers are required to present a valid electronic credential to access the reserved car 84. Thus, as travelers arrive at a scanner 86 on the platform 78 he or she touches, presses or operates the icon 72 to create and display an electronic token which is presented to the scanner 86 for scanning. Alternatively, the electronic token created for accessing the security service area 64 may be scanned. The electronic token for entering the security service area 64 has a finite life, for example, half an hour. It is contemplated by the present disclosure that the life of the electronic token for entering the security service area 64 may be any length of time in which a traveler may conveniently pass through the security checkpoint 200 and then board a reserved train car 84 without rushing.

The scanner 86 transmits the scanned token and/or data about the token, to the computer 12 which determines whether or not the token is valid. If valid, the computer 12 transmits a message to the scanner 86 indicating the token is valid and the traveler associated with the token is authorized to board the car 84. Thus, the traveler is permitted to board the car 84. Otherwise, if the token is invalid a message is transmitted to the scanner 86 indicating the token is invalid and authorization to board the car 84 is denied. Thus, the traveler is not permitted to board the car 84

Although the scanner 86 transmits the scanned token and/or data about the token to the computer 12 after scanning the electronic token, the scanner 86 may alternatively transmit the scanned token and/or data about the token to the computing device 10. Thus, it is contemplated by the present disclosure that the computing device 10 may alternatively determine whether or not the token is valid and as a result determine that the traveler is authorized or not authorized to board the car 84. The computing device 10 may also transmit a message to the scanner 86 indicating the traveler is authorized or not authorized to board the car 84. After receiving the message, the scanner 86 permits or does not permit a traveler to board the car 84 according to the message. Additionally, the computing device 10 and/or the scanner 86 may display a message indicating the traveler is authorized or not authorized to board the car 84.

Figure 9:
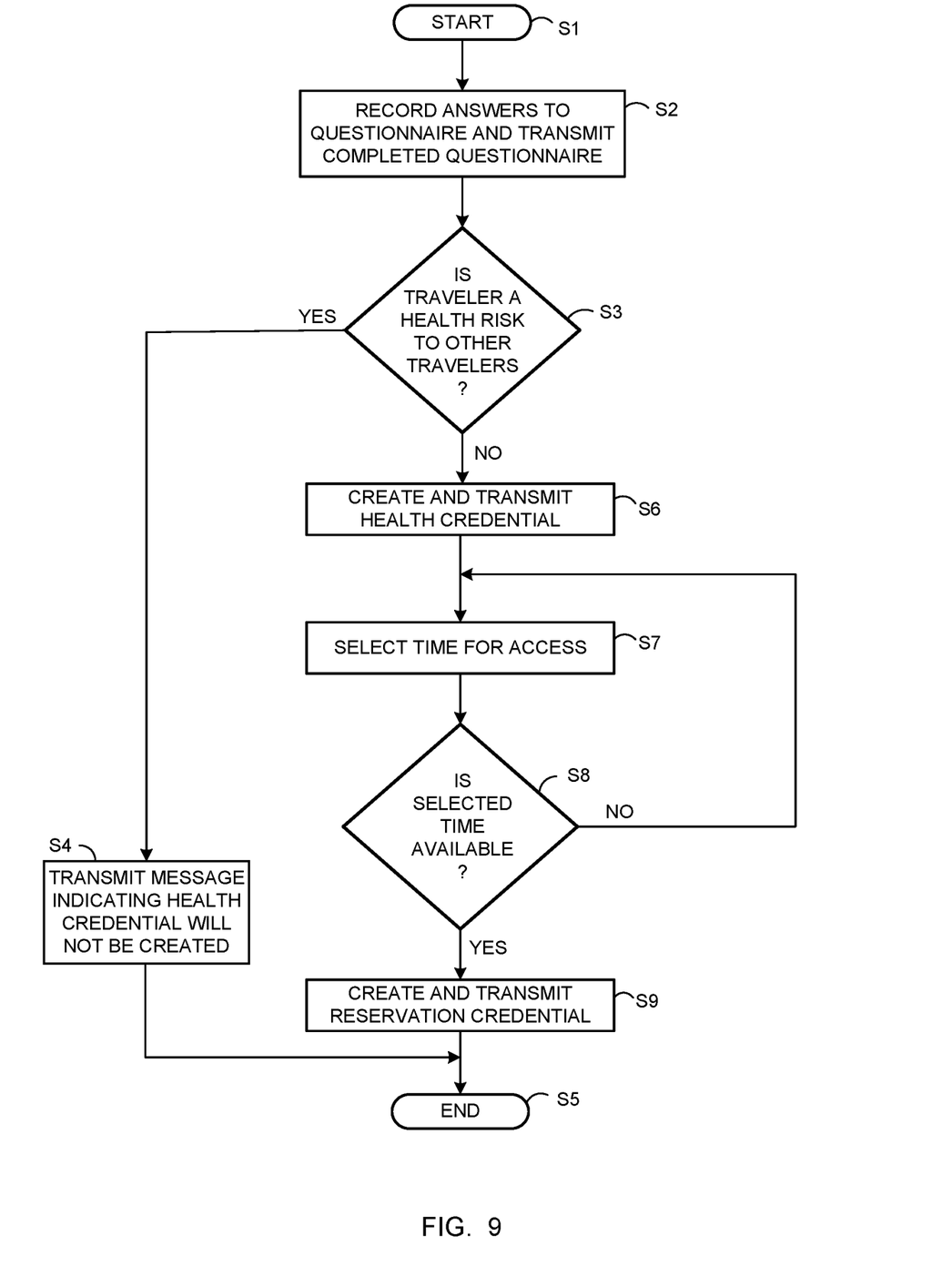
FIG. 9 is an example method and algorithm for creating a health credential and a reservation credential according to an embodiment of the present disclosure.

FIG. 9 is an example method and algorithm for creating a health credential and a reservation credential. FIG. 9 illustrates example operations performed when the processor 18 executes software stored in the memory 20 and the processor 34 executes software stored in the memory 36 to create a health credential and a reservation credential.

The method and algorithm start in step S1, then in step S2, the software executed by the processor 18 causes the computing device 10 to record answers to a health questionnaire entered by a traveler and transmit the completed questionnaire to the computer 12 via the network 16. In response to receiving the completed questionnaire, in step S3, the software executed by the processor 34 causes the computer 12 to determine if the traveler constitutes a health risk to others based on the completed questionnaire. The computer 12 determines a traveler does not constitute a health risk when the answers in the completed questionnaire evidence the traveler presents little or no risk of facilitating transmission of a pathogen to others.

Upon determining the traveler constitutes a health risk to others, in step S4, the computer 12 transmits via the network 16 to the computing device 10 a message indicating a health credential will not be created for the traveler. Next, in step S5, the method and algorithm end. However, upon determining the traveler does not constitute a health risk to other travelers, in step S6, the computer 12 creates a health credential and transmits the health credential to the computing device 10 via the network 16. The computing device 10 receives the health credential and stores the health credential in the memory 20.

In step S7, the software executed by the processor 18 causes the computing device 10 to record a time period selected by the traveler for accessing the security service area 64 and transmits the selected time period to the computer 12 using the network 16. In step S8, the software executed by the processor 34 causes the computer 12 to determine if the selected period of time is available by comparing the selected period against available periods of time. If the selected period is not available, in step S7, another period of time is selected. However, if the selected period is available, in step S9, the computer 12 creates a reservation credential and transmits via the network 16 the reservation credential to the computing device 10 for storage therein. Next, in step S5, the method and algorithm end.

Although the health credential is created and received by the computing device 10 before the reservation credential in the method and algorithm described herein with reference to FIG. 9, it is contemplated by the present disclosure that the reservation credential may be created and received before the health credential. Moreover, it is contemplated by the present disclosure that the time between receiving and storing the health credential in the computing device 10 and selecting a time for accessing the security service area 64 may be any period of time.

Figure 10:
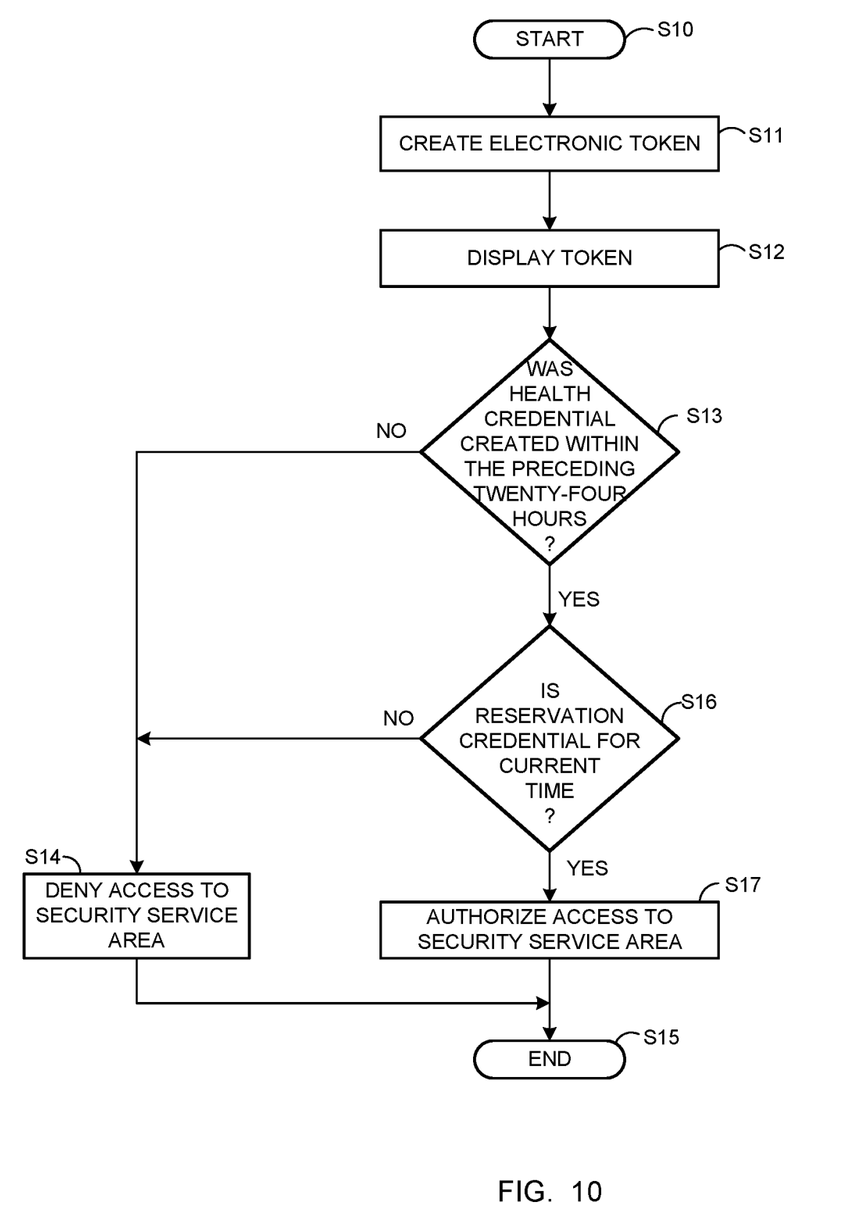
FIG. 10 is an example method and algorithm for enhancing authorization to access an area in a transportation hub according to an embodiment of the present disclosure.

FIG. 10 is an example method and algorithm for enhancing authorization to access an area in a transportation hub. FIG. 10 illustrates example operations performed when the processor 18 executes software stored in the memory 20 and the processor 34 executes software stored in the memory 36 for enhancing authorization to access an area within a transportation hub, for example, the security service area 64.

The method and algorithm start in step S10, and then in step S11 the software executed by the processor 18 causes the computing device 10 to create an electronic token for the traveler based on the traveler's health and reservation credentials created according to the method and algorithm described herein with reference to FIG. 9. More specifically, when the traveler arrives at the ACM 14, the traveler touches, presses or operates an icon displayed by the computing device 10 that causes the computing device 10 to create an electronic token based on the traveler's health and reservation credentials. The icon may be, for example, an icon that reads "Scan QR Code" or "Show QR Code" when the token is a QR code or "Scan the bar code" or "Show the Bar Code" when the token is a bar code. The electronic token may be any type of token, including, but not limited to, a QR code and a bar code. It is contemplated by the present disclosure that the token may include the traveler's email address, identifier of the computing device 10 associated with the traveler, and any other information relating to the traveler.

In step S12, the computing device 10 displays the electronic token for the ACM 14 to scan, and the ACM 14 transmits the scanned electronic token and/or data relating to the electronic token, to the computer 12 using the network 16. Next, in step S13, software executed by the processor 34 causes the computer 12 to determine whether or not the health credential for the traveler was created within the preceding twenty-four hours. If not, in step S14, the computer 12 determines the electronic token is invalid so the traveler is not authorized to access the security service area 64 and then, in step S15, the method and algorithm end. However, if the health credential was created within the preceding twenty-four hours, in step S16, the computer 12 determines whether or not the traveler's reservation credential is for the current time. If not, in step S14, the computer 12 determines the electronic token is invalid so the traveler is not authorized to access the security service area 64 and then, in step S15, the method and algorithm end. It is contemplated by the present disclosure that when the health credential or the reservation credential is invalid, a message may be displayed by the computing device 10 indicating the traveler is not authorized to access the security service area 64.

However, if the computer 12 determines that the reservation credential is for the current time, the electronic token is considered valid. A message indicating the traveler is authorized to access the security service area 64 may be displayed by the computing device 10. Next, in step S17, the user is authorized to access the security service area 64. Next, in step S15, the method and algorithm end.

Although the ACM 14 transmits the scanned token and/or data about the token to the computer 12 after scanning the electronic token in the method and algorithm described herein with regard to FIG. 10, the ACM 14 may alternatively transmit the scanned token and/or data about the token to the computing device 10. Thus, it is contemplated by the present disclosure that the computing device 10 may alternatively determine whether or not the token is valid and as a result that the traveler is authorized or not authorized to enter the security service area 64. The computing device 10 may transmit a message to the ACM 14 indicating the traveler is authorized or not authorized to access the security service area 64. After receiving the message, the ACM 14 operates the mechanism 66 according to the received message. Additionally, the computing device 10 may display a message indicating the traveler is authorized or not authorized to access the security service area 64.

Figure 11:
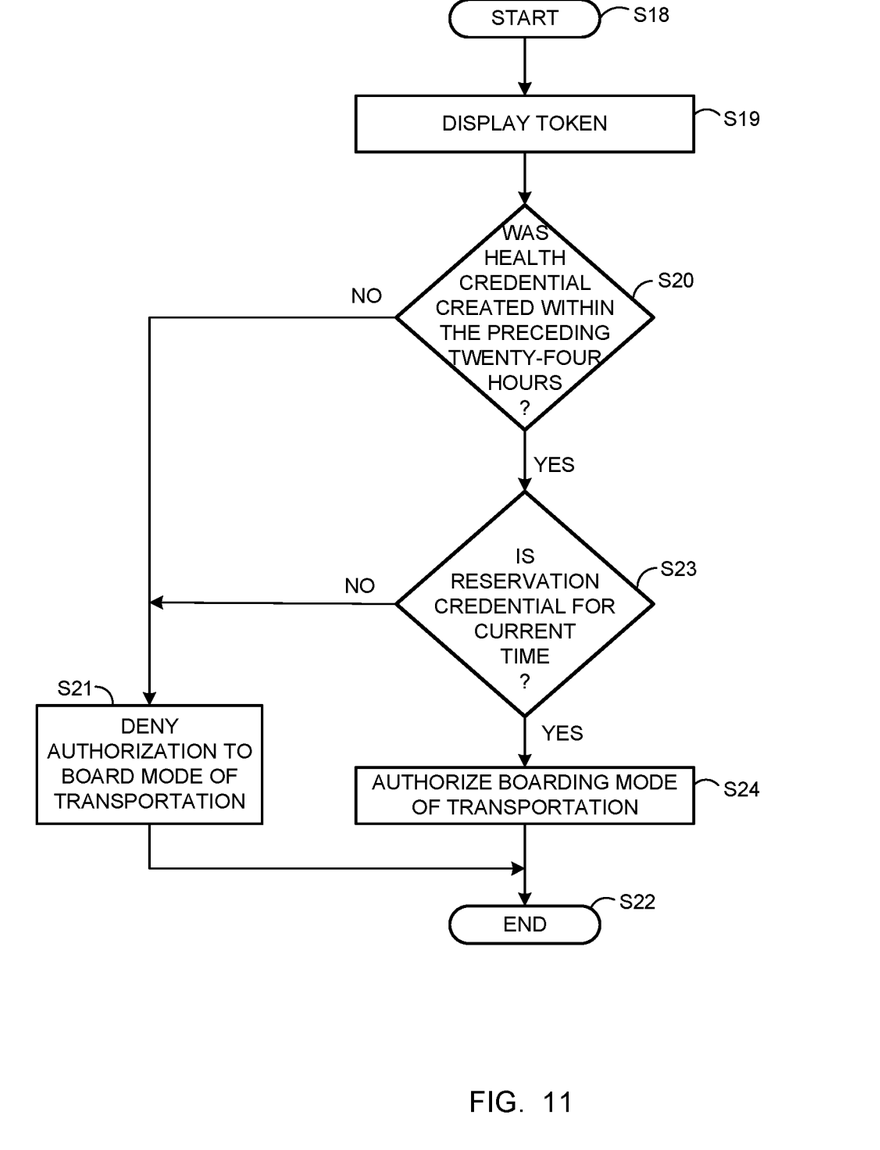
FIG. 11 is an example method and algorithm for enhancing authorization to access a mode of transportation in a transportation hub according to an embodiment of the present disclosure.

FIG. 11 is an example method and algorithm for enhancing authorization to access a mode of transportation in a transportation hub. FIG. 11 illustrates other example operations performed when the processor 18 executes software stored in the memory 20 and the processor 34 executes software stored in the memory 36 for enhancing authorization to access a mode of transportation in a transportation hub, for example, the train 80.

The method and algorithm start in step S18, and then in step S19 the software executed by the processor 18 causes the computing device 10 to display the electronic token created using the method and algorithm described herein with reference to FIG. 10. The electronic token is scanned by the ACM 14 which can transmit the scanned electronic token and/or data relating to the electronic token to the computer 12 using the network 16.

Next, in step S20, software executed by the processor 34 causes the computer 12 to determine whether or not the traveler's health credential was created within the preceding twenty-four hours. If not, in step S21, the computer 12 determines the health credential is invalid so the traveler is denied authorization to board the reserved train car 84 and then, in step S22, the method and algorithm end. However, if the health credential was created within the preceding twenty-four hours, in step S23, the computer 12 determines whether or not the traveler's reservation credential is for the current time. If not, in step S21, the computer 12 determines the electronic token is invalid so the traveler is denied authorization to board the reserved train car 84 and then, in step S22, the method and algorithm end. It is contemplated by the present disclosure that when the health credential or the reservation credential is invalid, a message may be displayed by the computing device 10 indicating the traveler is not authorized to board the reserved train car 84.

However, if the computer 12 determines that the reservation credential is for the current time, in step S24, the electronic token is deemed valid so the traveler is authorized to board the reserved train car 84. A message indicating the traveler is authorized to board the train 84 may be displayed by the computing device 10. Next, in step S22, the method and algorithm end.

Although the scanner 86 transmits the scanned token and/or data about the token to the computer 12 after scanning the electronic token in the method and algorithm described herein with reference to FIG. 11, the scanner 86 may alternatively transmit the scanned token and/or data about the token to the computing device 10. Thus, it is contemplated by the present disclosure that the computing device 10 may alternatively determine whether or not the token is valid and as a result determine that the traveler is authorized or not authorized to board the car 84. The computing device 10 may also transmit a message to the scanner 86 indicating the traveler is authorized or not authorized to board the car 84. After receiving the message, the scanner 86 permits or does not permit a traveler to board the car 84 according to the message. Additionally, the computing device 10 and/or the scanner 86 may display a message indicating the traveler is authorized or not authorized to board the car 84.

Although the health credential is deemed invalid if not created within the preceding twenty-four hours, it is contemplated by the present disclosure that the health credential may alternatively be created any period of time before scanning the electronic token by the ACM 14 that enables reducing traveler inconvenience and frustration and inhibits the spread of a pathogen like the coronavirus. Although the electronic token is created based on the health and reservation credentials as described herein, it is contemplated by the present disclosure that the electronic token may alternatively be created based on any type or combination of credentials and that such credentials may be created from information different than health and reservation information.

Using the methods and algorithms for enhancing authorization to access transportation hub services facilitates reducing travel delays and related traveler inconvenience and frustration, and facilitates reducing the risk that travelers will contract a pathogen like the coronavirus while traveling.

The example methods and algorithms described herein may be conducted entirely by the computing device 10, or partly on the computing device 10 and partly on the computer 12 using the network 16, or partly on the computing device 10, the computer 12 and the ACM 14 using the network 16. Moreover, the example methods described herein may be conducted entirely on other computer systems (not shown) other computing devices 10 (not shown). Thus, it should be understood that it is contemplated by the present disclosure that the example methods and algorithms described herein may be conducted on any combination of computers, computer systems, and computing devices 10 (not shown). Furthermore, data described herein as being stored in the memory 20 may alternatively be stored in any computer system (not shown) or computing device 10 (not shown) operable to communicate with the computing device 10 over the network 16. Additionally, the example methods described herein may be implemented with any number and organization of computer program components. Thus, the methods and algorithms described herein are not limited to specific computer-executable instructions. Alternative example methods and algorithms may include different computer-executable instructions or components having more or less functionality than described herein.

The example methods and/or algorithms described above should not be considered to imply a fixed order for performing the method and/or algorithm steps. Rather, the method and/or algorithm steps may be performed in any order that is practicable, including simultaneous performance of at least some steps. Moreover, the method and/or algorithm steps may be performed in real time or in near real time. It should be understood that, for any method and/or algorithm described herein, there can be additional, fewer, or alternative steps performed in similar or alternative orders, or in parallel, within the scope of the various embodiments, unless otherwise stated. Furthermore, the invention is not limited to the embodiments of the methods and/or algorithms described above in detail. Rather, other variations of the methods and/or algorithms may be utilized within the spirit and scope of the present disclosure.

What is claimed is:

1. A method for enhanced authorization to access transportation hub services comprising the steps of:
    creating, by an electronic device, a token based on a health credential and a reservation credential of a traveler;
    displaying the token by the electronic device;
    scanning the displayed token by an access control mechanism;
    transmitting data relating to the token to the electronic device;
    determining whether the credentials are valid based on the transmitted data;
    in response to determining the credentials are valid, authorizing the traveler to access a security service area in a transportation hub; and
    displaying the token by the electronic device after the traveler enters the security service area;
    scanning the displayed token by a scanner, the scanner being in a different location within the transportation hub than the access control mechanism;
    transmitting data relating to the token to the electronic device;
    determining whether the credentials are valid based on the transmitted data; and
    in response to determining the credentials are valid, authorizing the traveler to board a mode of transportation in the transportation hub.

2. The method according to claim 1, further comprising the steps of denying the traveler access to the security service area in response to determining the credentials are invalid.

3. The method according to claim 1, further comprising the step of denying the traveler authorization to board the mode of transportation in response to determining the credentials are invalid.

4. The method according to claim 3, said determining whether the credentials are valid step comprises determining the health credential was created less than a threshold time before scanning the token.

5. The method according to claim 4, wherein the threshold time is twenty-four hours.

6. The method according to claim 3, said determining whether the credentials are valid comprises determining the token was scanned within a period of time.

7. An electronic device for enhancing authorization to access transportation hub services comprising:
    a processor; and
    a memory configured to store data, said electronic device being associated with a network and said memory being in communication with said processor and having instructions stored thereon which, when read and executed by said processor, cause said electronic device to:

create a token based on a health credential and a reservation credentials of a traveler;
display the token;
receive from an access control mechanism that scanned the displayed token, data relating to the scanned token;
determine whether the credentials are valid based on the received data;
in response to determining the credentials are valid, authorize the traveler to access a security service area in a transportation hub;
display the token after the traveler enters the security service area;
receive from a scanner that scanned the displayed token, data relating to the scanned token, the scanner being in a different location within the transportation hub than the access control mechanism;
determine whether the credentials are valid based on the received data; and
in response to determining the credentials are valid, authorize the traveler to board a mode of transportation in the transportation hub.

8. An electronic device according to claim 7, the instructions when read and executed by the processor, further cause the electronic device to deny the traveler authorization to access the security service area in response to determining the credentials are invalid.

9. The electronic device according to claim 7, wherein the instructions when read and executed by the processor, further cause the electronic device to deny the traveler authorization to board the mode of transportation in response to determining the credentials are invalid.

10. The electronic device according to claim 7, wherein the health credential is valid when created less than a threshold time before the token is scanned.

11. The electronic device according to claim 10, wherein the threshold time is twenty-four hours.

12. The electronic device according to claim 7, wherein the reservation credential is valid when the token is scanned within a period of time.

13. A non-transitory computer-readable recording medium in an electronic device for enhancing authorization to access transportation hub services, the non-transitory computer-readable recording medium storing instructions which when executed by a hardware processor cause the non-transitory recording medium to perform steps comprising:
creating a token based on a health credential and a reservation credential of a traveler;
displaying the token;
receiving from an access control mechanism that scanned the displayed token, data relating to the scanned token;
determining whether the credentials are valid based on the received data;
in response to determining the credentials are valid, authorizing the traveler to access a security service area in a transportation hub;
in response to determining at least one of the credentials is invalid, denying the traveler access to the security service area;
displaying the token after the traveler enters the security service area;
receiving from a scanner that scanned the displayed token, data relating to the scanned token, the scanner being in a different location within the transportation hub than the access control mechanism;
determining whether the credentials are valid based on the received data; and
in response to determining the credentials are valid, authorizing the traveler to board a mode of transportation in the transportation hub.

14. The non-transitory computer-readable recording medium according to claim 13, wherein the instructions when read and executed by the hardware processor, cause the non-transitory recording medium to perform the step comprising denying the traveler authorization to access the security service area in response to determining the credentials are invalid.

15. The non-transitory computer-readable recording medium according to claim 13, wherein the instructions when read and executed by the hardware processor, cause the non-transitory recording medium to perform the step comprising denying the traveler authorization to board the mode of transportation in response to determining the credentials are invalid.

16. The non-transitory computer-readable recording medium according to claim 13, wherein the health credential is valid when created less than a threshold time before the token is scanned.

17. The non-transitory computer-readable recording medium according to claim 16, wherein the threshold time is twenty-four hours.

18. The non-transitory computer-readable recording medium according to claim 13, wherein the reservation credential is valid when the token is scanned within a period of time.

* * * * *